(12) United States Patent
Hayashi et al.

(10) Patent No.: US 8,759,598 B2
(45) Date of Patent: Jun. 24, 2014

(54) PRODUCTION PROCESS OF PROPYLENE

(75) Inventors: Mikio Hayashi, Kanagawa (JP);
Masashi Yamaguchi, Kanagawa (JP);
Yumiko Yoshikawa, Kanagawa (JP);
Takahiko Takewaki, Kanagawa (JP);
Tohru Setoyama, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 71 days.

(21) Appl. No.: 13/291,290

(22) Filed: Nov. 8, 2011

(65) Prior Publication Data

US 2012/0059139 A1 Mar. 8, 2012

Related U.S. Application Data

(63) Continuation of application No. PCT/JP2010/057632, filed on Apr. 28, 2010.

(30) Foreign Application Priority Data

May 8, 2009 (JP) ................................. 2009-113596

(51) Int. Cl.
*C07C 11/06* (2006.01)
*C07C 2/00* (2006.01)
*C07C 2/06* (2006.01)
*C07C 2/02* (2006.01)
*C07C 2/12* (2006.01)

(52) U.S. Cl.
USPC ........... 585/500; 585/502; 585/520; 585/530; 585/533; 502/60; 502/64

(58) Field of Classification Search
USPC ....................................................... 585/500
See application file for complete search history.

(56) References Cited

U.S. PATENT DOCUMENTS

| 6,388,161 | B1 * | 5/2002 | Dath et al. ..................... 585/648 |
| 7,332,640 | B2 | 2/2008 | Reyes et al. |
| 2004/0110629 | A1 * | 6/2004 | Stamires et al. ................. 502/60 |

FOREIGN PATENT DOCUMENTS

| CN | 85 1 02972 A | 10/1986 |
| CN | 1031834 A | 3/1989 |
| CN | 1305445 A | 7/2001 |
| CN | 1894177 A | 1/2007 |
| EP | 0490037 A1 * | 10/1991 |
| EP | 0841092 A2 * | 11/1997 |
| EP | 0841092 A2 | 5/1998 |
| JP | 10-151351 | 6/1998 |
| JP | 2007-509933 | 4/2007 |
| JP | 2007-291076 | 11/2007 |
| JP | 2007291076 A * | 11/2007 |
| WO | WO 2005/044763 A1 | 5/2005 |

OTHER PUBLICATIONS

Machine translated English document of JP 2007-291076A.*
JP 2007291076A English—Machine translated English document of JP 2007291076 A.*
International Search Report issued Jun. 22, 2010 in PCT/JP2010/057632 filed Apr. 28, 2010.
Toshihide Baba, et al.; "Shin Energy no Kaihatsu Part 2—Biomass Selective Synthesis of Propene by the Conversion of Ethene or Ethanol using SAPO-34"; Gekkan Fine Chemical, Mar. 15, 2008, vol. 37, No. 4, pp. 66-74.
U.S. Appl. No. 13/361,616, filed Jan. 30, 2012, Yamaguchi, et al.
Combined Office Action and Search Report issued Sep. 5, 2013 in Chinese Application No. 201080020934.1 (With English Translation and English Translation of Category of Cited Documents).

* cited by examiner

*Primary Examiner* — In Suk Bullock
*Assistant Examiner* — Youngsul Jeong
(74) *Attorney, Agent, or Firm* — Oblon, Spivak, McClelland, Maier & Neustadt, L.L.P.

(57) ABSTRACT

An object of the present invention is to provide a process of producing propylene by contacting ethylene with a catalyst, where propylene is produced with high selectivity. The present invention relates to a production process of propylene, comprising contacting ethylene with a catalyst, wherein the catalyst comprises a zeolite as an active ingredient and an acid content in the outer surface of the zeolite is 5 % or less based on an acid content of the entire zeolite.

9 Claims, No Drawings

PRODUCTION PROCESS OF PROPYLENE

CROSS-REFERENCE TO RELATED APPLICATIONS

This application is a Continuation of PCT/JP2010/057632 on Apr. 28, 2010. This application is based upon and claims the benefit of priority to Japanese Application No. 2009-113596 filed on May 8,2009, the contents of which are incorporated herein by reference.

BACKGROUND OF THE INVENTION

TECHNICAL FIELD

The present invention relates to a process for producing propylene with high selectivity by contacting ethylene with a catalyst.

BACKGROUND ART

Conventionally, a steam cracking process of naphtha or a fluid catalytic cracking process of vacuum gas oil is generally practiced as the process for producing propylene. However, the steam cracking process involves production of ethylene in a large amount other than propylene and is hardly allowed to largely change the production ratio between propylene and ethylene and therefore, it is difficult for this process to respond to change in the balance of supply and demand for propylene and ethylene.

Accordingly, a technique for producing propylene at a high yield by using only ethylene as the raw material is being demanded.

Patent Document 1 discloses a process for producing propylene from ethylene, wherein propylene can be produced by using aluminosilicate having a pore size of less than 0.5 nm for the catalyst.

PRIOR ART LITERATURE

Patent Document

[Patent Document 1] JP-A-2007-291076 (the term "JP-A" as used herein means an "published Japanese patent application")

SUMMARY OF THE INVENTION

Problems that the Invention is to Solve

However, as shown in Table 2 of Patent Document 1, there is a problem that with an increase in the concentration of ethanol/ethylene as raw materials, selectivity for propylene is decreased and selectivity for components having a carbon number of 4 or more (hereinafter referred to as a "$C_4$ or greater components"), specifically, selectivity for butene, selectivity for an olefin having a carbon number of 5 or more (hereinafter referred to as a "$C_5+$ olefin"), selectivity for an aromatic compound, and the like, is increased.

In consideration of the conventional technique above, an object of the present invention is to provide a process for producing propylene with high selectivity by using ethylene as the raw material while suppressing the selectivity for $C_4$ or greater components.

Means for Solving the Problems

As a result of intensive studies to attain the above-described object, the present inventors have found that when a zeolite in which the acid content in the outer surface is small for the acid content of the entirety is used as the catalyst, propylene can be produced with high selectivity from ethylene. The present invention has been accomplished based on this finding.

That is, the gist of the present invention resides in the followings.

<1> A production process of propylene, comprising contacting ethylene with a catalyst, wherein
said catalyst comprises a zeolite as an active ingredient, and
an acid content in the outer surface of the zeolite is 5% or less based on an acid content of the entire zeolite.

<2> The production process of propylene as described in <1> above, wherein the acid content in the outer surface of the zeolite is represented by a pyridine desorption amount defined by the following (I):

(I) a pyridine desorption amount per zeolite unit weight at 150 to 800° C. measured by a temperature-programmed desorption method at a temperature rising rate of 10° C./min on a pyridine-adsorbing zeolite that is obtained by drying a zeolite in vacuum at 500° C. for 1 hr as a pretreatment, contacting the pretreated zeolite with pyridine vapor at 150° C. to adsorb pyridine on the zeolite, and removing excess pyridine from the zeolite at 150° C. by exhausting under decompression and a helium flow.

<3> The production process of propylene as described in <1> or <2> above, wherein the acid content of the entire zeolite is represented by an ammonia desorption amount defined by the following (II):

(II) an ammonia desorption amount per zeolite unit weight at 100 to 800° C. measured by a temperature-programmed desorption method at a temperature rising rate of 10° C./min on an ammonia-adsorbing zeolite that is obtained by drying a zeolite under an a helium flow at 500° C. for 1 hr as a pretreatment, contacting the pretreated zeolite with 5 vol % ammonia/helium at 100° C. to adsorb ammonia on the zeolite, and contacting the obtained zeolite with steam at 100° C. to remove excess ammonia from the zeolite.

<4> The production process of propylene as described in any one of <1> to <3> above, wherein the zeolite has a pore size of less than 0.5 nm.

<5> The production process of propylene as described in any one of <1> to <4> above, wherein the zeolite has an oxygen 8-membered ring structure or an oxygen 9-membered ring structure.

<6> The production process of propylene as described in any one of <1> to <5> above, wherein the framework structure of the zeolite is a CHA-type structure.

<7> The production process of propylene as described in any one of <1> to <6> above, wherein the outer surface of the zeolite is silylated.

<8> The production process of propylene as described in any one of <1> to <6> above, wherein the zeolite is steam-treated.

<9> The production process of propylene as described in <8> above, wherein the temperature of the steam treatment is from 400 to 700° C.

<10> The production process of propylene as described in <8> or <9> above, wherein the zeolite is steam-treated after mixing with a compound containing an alkaline earth metal.

<11> A production process of polypropylene, comprising polymerizing propylene obtained by the production process described in any one of <1> to <10> above.

<12> A zeolite having a pore size of less than 0.5 nm, wherein an acid content in the outer surface is 5% or less based on an acid content of the entirety.

<13> The zeolite as described in <12> above, which is aluminosilicate.

<14> The zeolite as described in <12> or <13> above, which has an oxygen 8-membered ring structure or an oxygen 9-membered ring structure.

<15> The zeolite as described in any one of <12> to <14> above, which has a framework structure of CHA-type structure.

<16> The zeolite as described in any one of <12> to <15> above, which has a silylated outer surface.

<17> A catalyst comprising the zeolite described in any one of <12> to <16> above.

<18> A catalyst for the production of olefin, comprising the zeolite described in any one of <12> to <16> above.

ADVANTAGE OF THE INVENTION

According to the present invention, propylene can be produced with high selectivity by using ethylene as the raw material while suppressing the selectivity for $C_4$ or greater components.

MODE FOR CARRYING OUT THE INVENTION

Representative embodiments for carrying out the present invention are specifically described below, but the present invention is not limited to the following embodiments as long as its purport is conformed.

The production process of present invention is a process for producing propylene by contacting ethylene with a catalyst, wherein the catalyst comprises a zeolite as an active ingredient and the acid content in the outer surface of the zeolite is 5% or less based on the acid content of the entire zeolite.

The constituent components of the present invention are described below.

<Catalyst>

The catalyst for use in the present invention is first described. The catalyst for use in the present invention comprises, as an active ingredient, a zeolite. It is preferable that the active ingredient of the catalyst is a zeolite.

<Zeolite>

The zeolite indicates a crystalline material where $TO_4$ units (T is a central atom) having a tetrahedral structure are three-dimensionally connected by sharing an O atom to form open and regular micropores. The zeolite specifically includes silicates, phosphates, germanates and arsenates illustrated in the data book by Structure Commission of International Zeolite Association (IZA).

<Acid Content>

The acid content in the outer surface of the zeolite as used in the present invention (hereinafter sometimes simply referred to as an "outer surface acid content") indicates the total amount of acid sites present in the outer surface of the zeolite.

The outer surface acid content can be measured by allowing a substance capable of selectively adsorbing on acid sites of a zeolite and incapable of intruding into the inside of a micropore of the zeolite, to adsorb on a zeolite and quantitatively determining the adsorption amount. Although the substance above is not particularly limited, specifically, pyridine can be used.

The method for quantitatively determining the pyridine adsorption amount is not particularly limited, but the adsorption amount can be measured usually by the following procedure. A zeolite is dried as a pretreatment and then contacted with and caused to adsorb pyridine vapor, and excess pyridine is removed to obtain a pyridine-adsorbing zeolite. The pyridine desorption amount per unit weight of the pyridine-adsorbing zeolite is measured by a temperature-programmed desorption method (hereinafter sometimes referred to as "TPD"), whereby the outer surface acid content can be determined.

The outer surface acid content is not particularly limited but is usually 0.6 mmol/g or less, preferably 0.3 mmol/g or less. If the acid content exceeds the upper limit above, a non-shape selective reaction may take place on the outer surface to decrease the selectivity for propylene.

The acid content of the entire zeolite in the present invention (hereinafter sometimes simply referred to as an "entirety acid content") is an acid content of the entire zeolite and specifically indicates the total of acid contents in the outer surface and in the inside of micropores.

The acid content of the entire zeolite can be measured by allowing a substance capable of selectively adsorbing on acid sites of a zeolite and intruding also into the inside of a micropore, to adsorb on a zeolite and quantitatively determining the adsorption amount. Although the substance above is not particularly limited, specifically, ammonia can be used.

The method for quantitatively determining the ammonia adsorption amount is not particularly limited, but the adsorption amount can be measured usually by the following procedure. A zeolite is dried as a pretreatment and then contacted with and caused to adsorb ammonia, and excess ammonia is removed to obtain an ammonia-adsorbing zeolite. The ammonia desorption amount per unit weight of the ammonia-adsorbing zeolite is measured by a temperature-programmed desorption method, whereby the entirety acid content can be determined.

The entirety acid content is not particularly limited but is usually 4.8 mmol/g or less, preferably 2.8 mmol/g or less, and usually 0.15 mmol/g or more, preferably 0.30 mmol/g or more. If the acid content exceeds the upper limit above, this tends to bring about rapid deactivation due to coke deposition, cause aluminum to readily drop off from the framework (so-called dealumination), or weaken the acid strength per acid site, whereas if it is less than the lower limit, since the acid content is little, the ethylene conversion may decrease.

In the zeolite for use in the present invention, the acid content in the outer surface of the zeolite is 5% or less, preferably 4.5% or less, more preferably 3.5% or less, based on the acid content of the entire zeolite. The lower limit is not particularly limited and is preferably lower, but the lower limit is usually 0.1% or more.

If the outer surface acid content exceeds the upper limit above based on the entirety acid content, there arises a problem that selectivity for propylene decreases due to a side reaction occurring in the outer surface of the zeolite. The reason therefor is considered because the reaction in the outer surface is free from shape-selective restrictions and a product of $C_4$ or greater components is produced. Also, propylene produced in a micropore of the catalyst again acts with the outer surface acid site and brings about a side reaction, which is considered to cause reduction in the propylene selectivity.

<Structure>

The zeolite for use in the present invention usually has a micropore.

The pore size of the zeolite for use in the present invention is not particularly limited and is preferably smaller, but the pore size (length) is usually less than 0.5 nm, preferably 0.4 nm or less. If the pore size (length) of the zeolite exceeds the upper limit above, by-products (e.g., butene, pentene) other than propylene are disadvantageously produced in large amounts, and propylene cannot be produced in a high selectivity from ethylene in some cases.

The pore size as used herein indicates the Crystallographic free diameter of the channels set by International Zeolite Association (IZA). The "pore size of less than 0.5 nm" means that when the micropore is in a true circle shape, the diameter is less than 0.5 nm and when the micropore is in an elliptic shape, the short diameter is less than 0.5 run.

The mechanism for enabling production of propylene in a high selectivity from ethylene by using a zeolite with a small pore size is not elucidated in detail, but it is considered that ethylene can be activated by strong acid sites present in the zeolite and propylene can be selectively produced thanks to the small pore size. That is, the pore size is small, but the objective propylene produced resulting from contact with the zeolite can exit from the micropore. However the $C_4$ or greater components such as butene and pentene produced as by-products are presumed to remain in the micropore because of their excessively large molecules. Such a mechanism is thought to enable the production of propylene with high selectivity.

Incidentally, the lower limit of the pore size of the zeolite is not particularly limited but is usually 0.2 nm or more, preferably 0.3 nm or more.

If the pore size is less than the lower limit above, it may result that both ethylene and propylene cannot pass through the micropore and action of ethylene with an active site scarcely occurs to decrease the reaction rate.

The zeolite for use in the present invention is not particularly limited, but usually, those having an oxygen 8-membered ring structure or a 9-membered ring structure are preferred.

The oxygen 8-membered ring structure or 9-membered ring structure means a ring structure where a micropore of the zeolite consists of 8 or 9 $TO_4$ units (T is Si, P, Ge, Al, Ga or the like). When it has an oxygen 8-membered ring structure or an oxygen 9-membered ring structure, a preferable pore size is obtained, and a higher selectivity of propylene is obtained.

Above all, a zeolite where the micropore is composed of only an oxygen 8-membered ring is preferred.

Specific examples of the framework structure of the zeolite where the micropore is composed of only an oxygen 8-membered ring include, as expressed in the code assigned by the International Zeolite Association (IZA), AFX, CAS, CHA, DDR, ERI, ESV, GIS, GOO, ITE, JBW, KFI, LEV, LTA, MER, MON, MTF, PAU, PHI, RHO, RTE and RTH.

Specific examples of the zeolite containing an oxygen 9-membered ring and having only micropores of oxygen 9- or smaller membered ring include, as expressed in the code assigned by the International Zeolite Association (IZA), NAT, RSN and STT.

Out of these framework structures, preferred examples of the framework structure of the zeolite for use in the present invention include AFX, CHA, DDR, ERI, LEV, RHO and RTH, with CHA being more preferred.

The framework density of the zeolite for use in the present invention is not particularly limited, but in general, the framework density of the zeolite is preferably 18.0 T/nm$^3$ or less, more preferably 17.0 T/nm$^3$ or less, and is usually 13.0 T/nm$^3$ or more, preferably 14.0 T/nm$^3$ or more.

The "framework density (unit: T/nm$^3$)" as used herein means the number of T atoms (out of atoms constituting the framework of a zeolite, atoms except for oxygen) present per unit volume (1 nm$^3$) of the zeolite, and this value is determined by the structure of the zeolite.

The framework of the zeolite for use in the present invention usually contains a metal. The metal contained is not particularly limited but is usually at least one member selected from aluminum, gallium, iron and boron, preferably aluminum.

As to the catalyst with the active ingredient being the zeolite for use in the present invention, a proton exchange catalyst is usually used, and a part thereof may be exchanged by an alkali metal such as Na and K or an alkaline earth metal such as Mg and Ca.

The $SiO_2/M_2O_3$ molar ratio (hereinafter referred to as an "$SiO_2$/metal molar ratio"; M is a trivalent metal such as aluminum, gallium, iron and boron) of the zeolite for use in the present invention is not particularly limited but is usually 5 or more, preferably 10 or more. If the $SiO_2$/metal molar ratio is less than the lower limit above, durability of the catalyst may deteriorate. The upper limit of the $SiO_2$/metal molar ratio is not particularly limited but is usually 1,000 or less. If the $SiO_2$/metal molar ratio exceeds this upper limit, the catalytic activity is sometimes reduced.

Specific examples of the zeolite for use in the present invention include aluminosilicate composed of silicon and aluminum as constituent elements, aluminophosphate (ALPO) composed of aluminum and phosphorus, and silicoaluminophosphate (SAPO) composed of silicon, aluminum and phosphorus. Among these, aluminosilicate and silicoaluminophosphate are preferred, and aluminosilicate is more preferred.

The zeolite for use in the present invention is preferably a zeolite of CHA structure. Specific examples of the zeolite of CHA structure include aluminosilicate composed of silicon and aluminum as constituent elements, aluminophosphate (ALPO-34) composed of aluminum and phosphorus, and silicoaluminophosphate (SAPO-34) composed of silicon, aluminum and phosphorus. Among these, aluminosilicate and silicoaluminophosphate are preferred, and aluminosilicate is more preferred.

The $SiO_2/Al_2O_3$ molar ratio in the aluminosilicate is not particularly limited but is usually 5 or more, preferably 10 or more. If the molar ratio is less than the lower limit above, this tends to bring about rapid deactivation due to coke decomposition, cause aluminum to readily drop off from the framework (so-called dealumination), or weaken the acid strength per acid site. Also, the $SiO_2/Al_2O_3$ molar ratio is usually 200 or less, preferably 100 or less. If the molar ratio exceeds this upper limit, since the acid content is little, the ethylene conversion may decrease.

<Production Process>

The zeolite for use in the present invention is not particularly limited in its production process and may be produced by a known method, for example, by the production process described in U.S. Pat. No. 4,544,538. The zeolite can be generally prepared by a hydrothermal synthesis method. Also, a zeolite changed in the composition through ion exchange, dealumination treatment, impregnation or the like after the hydrothermal synthesis may be used.

<Method for Reducing the Ratio of Outer Surface Acid Content Based on Entirety Acid Content>

The zeolite for use in the present invention is a zeolite where the acid content in the outer surface of the zeolite is 5% or less based on the acid content of the entire zeolite, and this can be obtained by reducing the ratio of the outer surface acid content of a normal zeolite.

The method for reducing the ratio of the outer surface acid content based on the entirety acid content is not particularly limited but includes 1) a method of silylating the outer surface of a zeolite, 2) a method of applying a steam treatment (steaming) to a zeolite, and 3) a method of treating a zeolite with a dicarboxylic acid.

<Silylation>

The method of silylating the outer surface of a zeolite is a method for reducing the outer surface acid content by silylating the outer surface of a zeolite that is an active ingredient of the catalyst. The method for silylation is not particularly limited, and a known method can be appropriately used. Specifically, the silylation can be performed, for example, by liquid phase silylation using alkoxysilane or by vapor phase silylation using chlorosilane.

The silylating agent is not particularly limited, but specific examples of the alkoxysilane include a quaternary alkoxysilane such as tetramethoxysilane and tetraethoxysilane; a tertiary alkoxysilane such as trimethoxymethylsilane and triethoxymethylsilane; a secondary alkoxysilane such as dimethoxydimethylsilane and diethoxydimethylsilane; and a primary alkoxysilane such as methoxytrimethylsilane and ethoxytrimethylsilane. Specific examples of the chlorosilane that can be used include chlorosilanes such as tetrachlorosilane, dimethyldichlorosilane and trimethylchlorosilane. Among these, tetraethoxysilane is preferred as the alkoxysilane, and tetrachlorosilane is preferred as the chlorosilane.

In the liquid phase silylation method, a solvent can be appropriately used. The solvent used is not particularly limited, but an organic solvent such as benzene, toluene and hexamethyldisiloxane, or water can be used. In the liquid phase silylation method, the quantitative ratio of silylating agent/zeolite (mol/mol) in the treating solution is not particularly limited but is usually 5 or less, preferably 3 or less, and usually 0.005 or more, preferably 0.1 or more. If this value exceeds the upper limit above, the micropore is sometimes blocked due to excessive silylation, whereas if it is less than the above-described lower limit, insufficient silylation may result, failing in poisoning the acid sites on the outer surface. The silylation temperature can be appropriately adjusted according to the kind of the silylating agent or solvent and is not limited, but the silylation temperature is usually 140° C. or less, preferably 120° C. or less, and usually 20° C. or more, preferably 40° C. or more. If the silylation temperature exceeds the upper limit above, silylation may not occur efficiently due to evaporation of the silylating agent, whereas if it is less than the above-described lower limit, the silylation reaction sometimes proceeds at a low rate. The treatment time is not particularly limited as long as it is long enough to allow for progress of silylation where the object of the present invention can be achieved, but the treatment time is usually 0.5 hours or more, preferably 2 hours or more. The treatment time has no particular upper limit but is usually 48 hours or less. If the treatment time is less than the lower limit above, silylation may not proceed sufficiently, resulting in insufficient poisoning of acid sites.

The vapor phase silylation treatment is performed for a normal zeolite such that the weight of silica deposited becomes usually 20 wt % or less, preferably 18 wt % or less. The weight of silica deposited has no particular lower limit but is usually 0.1 wt % or more, preferably 1 wt % or more. If the weight of silica deposited exceeds the upper limit above, the micropore may be blocked due to excessive silylation, whereas if it is less than the above-described lower limit, insufficient silylation may result, failing in poisoning the acid sites on the outer surface.

The temperature of vapor phase silylation can be appropriately adjusted according to the silylating agent and is not limited, but the temperature is usually 20° C. or more, preferably 100° C. or more, and usually 500° C. or less, preferably 400° C. or less. If the temperature exceeds the upper limit above, decomposition of the silylating agent, collapse of the zeolite framework, and the like may occur, whereas if it is less than the above-described lower limit, the silylation reaction does not proceed in some cases.

<Steam Treatment>

The method for steaming a zeolite is not particularly limited, but the steaming temperature is usually 400° C. or more, preferably 500° C. or more, and usually 700° C. or less, preferably 650° C. or less. If the temperature is less than the lower limit above, the effect created by steaming is small, whereas if it exceeds the above-described upper limit, collapse of the zeolite framework may occur.

The steam may also be used by diluting it with an inert gas such as helium and nitrogen. The steam concentration is not particularly limited but is usually 3 vol % or more, preferably 5 vol % or more. The steam concentration has no upper limit, and the treatment can be performed with 100% steam.

The zeolite can also be physically mixed with an alkaline earth metal-containing compound before steaming. The alkaline earth metal-containing compound includes calcium carbonate, calcium hydroxide and magnesium carbonate, with calcium carbonate being preferred.

The amount of the alkaline earth metal-containing compound is preferably from 0.5 to 45 wt %, more preferably from 3 to 40 wt %, based on the zeolite.

Also, the steaming may be performed in a state where an organic material is caused to exist in the inside of the micropore so as to selectively reduce the outer surface acid content by dealumination. The organic material is not particularly limited but includes a structure regulating agent used at the synthesis of zeolite, and coke produced by the reaction. Out of these organic materials, the structure regulating agent is present in a synthesized state in the micropore of zeolite, and the coke may be caused to exist in the inside of the micropore by a method of, for example, flowing hydrocarbon into the catalyst at a temperature of 200° C. or more.

<Treatment with Dicarboxylic Acid>

The method for treating a zeolite with a dicarboxylic acid is not particularly limited as long as the object of the present invention can be achieved. The dicarboxylic acid is considered to reduce the acid content by promoting elimination from the skeleton of a metal in the framework, such as dealumination of zeolite, and thanks to its large molecular size as compared with the zeolite micropore, the dicarboxylic acid cannot intrude into the micropore and in turn, can selectively reduce the acid content in the outer surface.

Examples of the dicarboxylic acid include oxalic acid, malonic acid, succinic acid, glutaric acid, adipic acid, maleic acid, phthalic acid, isophthalic acid, fumaric acid and tartaric acid. Such acids may be used by mixing them. Among these dicarboxylic acids, oxalic acid is preferred.

The dicarboxylic acid is preferably mixed with zeolite after dissolving it in a solvent such as alcohol and water to form a solution. The concentration of the dicarboxylic acid in the solution is generally from 0.01 to 4 M, preferably from 1 to 3 M. The temperature at the mixing is usually from 15 to 95° C., preferably from 50 to 85° C. The mixing with zeolite may be performed two or more times so as to accelerate the dealumination of the zeolite surface.

Also, the treatment with a dicarboxylic acid may be performed in a state where an organic materials is caused to exist in the inside of the micropore so as to selectively reduce the acid content in the outer surface by dealumination. The organic material is not particularly limited but includes a structure regulating agent used at the synthesis of zeolite, and coke produced by the reaction. Out of these organic materials, the structure regulating agent is present in a synthesized state in the micropore of zeolite, and the coke may be caused to exist in the inside of the micropore by a method of, for example, flowing hydrocarbon into the catalyst at a temperature of 200° C. or more.

The catalytic active ingredient above may be directly used as a catalyst for the reaction or may be granulated/molded using a substance or binder inert to the reaction or mixed with such a substance and then used for the reaction. In this connection, the outer surface acid content based on the entirety acid content can be reduced also by molding. Examples of the substance or binder inert to the reaction include alumina or alumina sol, silica, silica gel, quartz, and a mixture thereof. The method of reducing the acid content by molding includes, for example, a method of connecting an acid site on the surface of zeolite with a binder, or likes.

Incidentally, in the case of using a binder having an acid site, such as alumina, the acid content measured by the above-described method for measuring the outer surface acid content and the entirety acid content is a total value including the acid content of the binder together with the acid content of zeolite. In such a case, the acid content of the binder is determined by a different method and the value is subtracted from the total value, whereby the outer surface acid content or entirety acid content not including the acid content of the binder can be determined. The method for determining the acid content of the binder is not particularly limited, but examples thereof include a method where the acid content of the entire zeolite is determined from the peak intensity of tetradentate Al derived form the zeolite acid site in $^{27}$Al-NMR and the obtained value is subtracted from the total value of the acid content of entire zeolite and the acid content of binder, determined by an ammonia temperature-programmed desorption method.

The present invention relates to a process for producing propylene by contacting ethylene with a catalyst and thereby causing a reaction. The reaction method is described below.

(1) Reaction Method

<Reaction Raw Material>

The ethylene as the raw material is not particularly limited, and ethylene obtained by various known processes, such as ethylene produced from a petroleum-derived source by a catalytic cracking process, a steam cracking process or the like, ethylene obtained by a Fischer-Tropsch process using as the raw material a hydrogen/CO mixed gas resulting from gasification of coal, ethylene obtained by dehydrogenation or oxidative dehydrogenation of ethane, ethylene obtained by a metathesis reaction and a homologation reaction of propylene, ethylene obtained by an MTO (Methanol-to-Olefin) reaction, ethylene obtained by dehydration of ethanol, and ethylene obtained by oxidative coupling of methane, may be arbitrarily used. At this time, ethylene in a state of being optionally mixed with other compounds attributable to various production processes may be used as it is, or purified ethylene may be used. Purified ethylene is preferred.

Incidentally, thanks to acid sites present in the zeolite, ethanol is readily dehydrated and converted into ethylene. Therefore, the reaction referred to in the present invention can also be performed by directly introducing ethanol as the raw material into the reactor.

In producing propylene by the process of the present invention, an olefin contained in the reactor outlet gas may be recycled.

The olefin recycled is usually ethylene, but other olefins may be recycled. The olefin as the raw material is preferably a lower olefin. A branched olefin can hardly intrude into the zeolite micropore due to its molecular size and is not preferred. The olefin is preferably ethylene or linear butene, and most preferably ethylene.

<Reactor>

Ethylene for use in the present invention is preferably contacted with the catalyst in a reactor to produce propylene. The form of the reactor used is not particularly limited, but a continuous fixed-bed reactor or a fluidized-bed reactor is usually selected. A fluidized-bed reactor is preferred.

At the time of packing the above-described catalyst in a fluidized bed reactor, a particulate material inert to reaction, such as quartz sand, alumina, silica and silica-alumina, may be mixed with the catalyst and packed so as to keep narrow the temperature distribution of the catalyst layer. In this case, the amount used of the particulate material inert to reaction, such as quartz sand, is not particularly limited. Incidentally, in view of uniform mixing with the catalyst, the particulate material preferably has about the same particle size as the catalyst.

<Diluent>

In addition to ethylene, a gas inert to reaction, such as helium, argon, nitrogen, carbon monoxide, carbon dioxide, hydrogen, water, paraffins, hydrocarbons (e.g., methane), aromatic compounds and a mixture thereof, may be allowed to exist in the reactor. Above all, water (steam) is preferably present together.

(2) Reaction Conditions

<Substrate Concentration>

The concentration of ethylene (that is, the substrate concentration) in all feed components supplied to the reactor is not particularly limited, but the concentration of ethylene in all feed components is usually 90 mol % or less, preferably 70 mol % or less, and usually 5 mol % or more. If the substrate concentration exceeds the upper limit above, significant production of aromatic compounds or paraffins results and the selectivity of propylene is liable to decrease. If the substrate concentration is less than the above-described lower limit, the reaction proceeds at a low rate and requires a large amount of catalyst, and the reactor size tends to become excessively large.

Accordingly, the ethylene is preferably diluted with a diluent described below to give such a substrate concentration, if desired.

<Space Velocity>

The space velocity as used herein indicates a flow rate (weight/hour) of ethylene as the reaction raw material per weight of the catalyst (catalytic active ingredient). Here, the weight of the catalyst is the weight of the catalytic active ingredient, excluding the inert component or binder used for the granulation/molding of the catalyst.

The space velocity is not particularly limited but is preferably from 0.01 $Hr^{-1}$ to 500 $Hr^{-1}$, more preferably from 0.1 $Hr^{-1}$ to 100 $Hr^{-1}$. If the space velocity is excessively high, the proportion of ethylene in the reactor outlet gas is increased to lower the yield of propylene and this is not preferred, whereas if the space velocity is too low, undesired by-products such as paraffins are produced and the selectivity of propylene is disadvantageously lowered.

<Reaction Temperature>

The reaction temperature is not particularly limited as long as propylene is produced by the contact of ethylene with the catalyst, but the reaction temperature is usually about 200° C. or more, preferably 300° C. or more, and usually 700° C. or less, preferably 600° C. or less. If the reaction temperature is less than the lower limit above, the reaction proceeds at a low rate and this tends to cause remaining of the unreacted raw material in a large amount and furthermore, decrease the yield of propylene. On the other hand, if the reaction temperature exceeds the above-described upper limit, the yield of propylene is sometimes extremely decreased.

<Reaction Pressure>

The reaction pressure is not particularly limited but is usually 2 MPa (absolute pressure, hereinafter the same) or less, preferably 1 MPa or less, more preferably 0.7 MPa or less, and usually 1 kPa or more, preferably 50 kPa or more. If the reaction pressure exceeds the upper limit above, the production of undesired by-products such as paraffins is increased and the selectivity of propylene is liable to decrease, whereas if the reaction pressure is less than the above-described lower limit, the reaction tends to proceed at a low rate.

<Conversion Ratio>

In the present invention, the conversion ratio is not particularly limited, but the reaction is preferably performed under the conditions of giving an ethylene conversion of usually 20% or more, preferably 40% or more, more preferably 50% or more, and usually 95% or less, preferably 90% or less.

If this conversion ratio is less than the lower limit above, a large proportion of unreacted ethylene and a low yield of propylene may disadvantageously result, whereas if it exceeds the above-described upper limit, this may bring about an increase in the production of undesired by-products such as paraffins and a decrease in the selectivity of propylene and is not preferred.

In the case of performing the reaction in a fluidized-bed reactor, the reaction can be operated at a preferred conversion ratio by adjusting the residence time of catalyst in the reactor and the residence time in a regenerator.

The conversion ratio is a value calculated according to the following formula:

Ethylene conversion (%)=[[ethylene (mol) at the inlet of reactor−ethylene (mol) at the outlet of reactor)]/ethylene (mol) at the inlet of reactor]×100

<Selectivity>

The selectivity as used in the present specification is a value calculated by each of the following formulae. In the following formulae, propylene, butene, $C_5^+$, paraffin or aromatic compound-derived carbon (mol) means the number of moles of carbon atoms constituting each component. Incidentally, the paraffin is the total of paraffins having a carbon number of 1 to 3, the aromatic compound is the total of benzene, toluene and xylene, and $C_5+$ is the total of $C_5$ or more hydrocarbons excluding the aromatic compound above.

Propylene selectivity (%)=[propylene-derived carbon (mol) at the outlet of reactor/[entire carbon (mol) at the outlet of reactor−ethylene-derived carbon (mol) at the outlet of reactor]]×100

Butene selectivity (%)=[butene-derived carbon (mol) at the outlet of reactor/[entire carbon (mol) at the outlet of reactor−ethylene-derived carbon (mol) at the outlet of reactor]]×100

$C_5$+selectivity (%)=[$C_5$+-derived carbon (mol) at the outlet of reactor/[entire carbon (mol) at the outlet of reactor−ethylene-derived carbon (mol) at the outlet of reactor]]×100

Paraffin selectivity (%)=[paraffin-derived carbon (mol) at the outlet of reactor/[entire carbon (mol) at the outlet of reactor−ethylene-derived carbon (mol) at the outlet of reactor]]×100

Aromatic compound selectivity (%)=[aromatic compound-derived carbon (mol) at the outlet of reactor/[entire carbon (mol) at the outlet of reactor−ethylene-derived carbon (mol) at the outlet of reactor]]×100

The yield in the present specification is obtained by a product of the ethylene conversion above and the selectivity of each component formed, for example, specifically, propylene yield is a value represented by the following formula.

Propylene yield (%)=[Ethylene conversion (%)×Propylene selectivity (%)]/100.

(3) Reaction Product

As for the reactor outlet gas (reactor effluent), a mixed gas containing propylene as the reaction product, unreacted ethylene, by-products and diluent is obtained. The propylene concentration in the mixed gas is usually 1 wt % or more, preferably 2 wt % or more, and usually 95 wt % or less, preferably 80 wt % or less.

This mixed gas usually contains ethylene, and at least a part of the ethylene in the mixed gas is preferably recycled to the reactor and reused as the reaction raw material.

The by-product includes olefins with a carbon number of 4 or more and paraffins.

The propylene obtained by the present invention is polymerized, whereby polypropylene can be produced. The method for polymerization is not particularly limited, but the obtained propylene can be used by directly introducing it as a raw material of the polymerization system. The propylene can also be used as a raw material of other propylene derivatives. For example, an acrylonitrile can be produced by ammonia oxidation; an acrolein, an acrylic acid and an acrylic acid ester can be produced by selective oxidation; an oxoalcohol such as n-butyl alcohol and 2-ethylhexanol can be produced by oxoreaction; and a propylene oxide and a propylene glycol can be produced by selective oxidation. In addition, acetone can be produced by Wacker reaction, and methyl isobutyl ketone can be produced from the acetone. Also, acetone cyanhydrin can be produced from acetone, and this is finally converted into methyl methacrylate. An isopropyl alcohol can also be produced by propylene hydration. Furthermore, phenol, bisphenol A or polycarbonate resin can be produced by reacting propylene with benzene to produce cumene and using the cumene as the raw material.

EXAMPLES

The present invention is described in greater detail below by referring to Examples, but the present invention is not limited to the following Examples as long as its purport is conformed.

<Preparation of Catalyst>

Preparation Example 1

A proton-type aluminosilicate ($SiO_2/Al_2O_3$=37 (by mol), pore size: 0.38 nm) having a CHA structure was subjected to silylation with tetraethoxysilane. That is, 10 ml of hexamethyldisiloxane as the solvent and 5 ml of tetraethoxysilane as the silylating agent were added to 1 g of aluminosilicate, and a reflux treatment was performed at 100° C. with stirring for 6 hours. After the treatment, the solid solution was separated by filtration, and the obtained aluminosilicate was dried at 100° C. for 2 hours.

Preparation Example 2

A proton-type aluminosilicate ($SiO_2/Al_2O_3$=37 (by mol), pore size: 0.38 nm) having a CHA structure was subjected to silylation with dimethoxydimethylsilane. That is, 10 ml of hexamethyldisiloxane as the solvent and 5 ml of dimethoxydimethylsilane as the silylating agent were added to 1 g of aluminosilicate, and a reflux treatment was performed at 100° C. with stirring for 6 hours. After the treatment, the solid solution was separated by filtration, and the obtained aluminosilicate was dried at 100° C. for 2 hours.

Preparation Example 3

A proton-type aluminosilicate ($SiO_2/Al_2O_3=37$ (by mol), pore size: 0.38 nm) having a CHA structure was subjected to steaming. That is, a gas having a composition containing 30 vol % of steam and 70 vol % of nitrogen was flowed to the aluminosilicate at 600° C. for 6 hours.

Preparation Example 4

A proton-type aluminosilicate ($SiO_2/Al_2O_3=37$ (by mol), pore size: 0.38 nm) having a CHA structure was physically mixed with calcium carbonate and then subjected steaming. That is, calcium carbonate was mixed in a ratio of 36 wt % based on the zeolite, and a gas having a composition containing 30 vol % of steam and 70 vol % of nitrogen was flowed to the physical mixture of aluminosilicate and calcium carbonate at 600° C. for 6 hours.

Preparation Example 5

For comparison to Preparation Examples 1 to 4, a proton-type aluminosilicate ($SiO_2/Al_2O_3=37$ (by mol), pore size: 0.38 nm) having a CHA structure was prepared as an untreated catalyst.

Examples 1 to 6 and Comparative Example 1

<Measurement of Acid Content>

With respect to aluminosilicates of Preparation Example 1 to 5, each of the entirety acid content and the outer surface acid content was measured by $NH_3$-TPD and Pyridine-TPD. The measurement was performed as follows by using Automatic temperature-programed desorption analyzer TP5500 manufactured by BEL Japan, Inc.

(Entirety Acid Content)

After allowing the specimen aluminosilicate in an amount of 30 to 50 mg to stand and dry at 500° C. for 1 hour in a helium atmosphere, adsorbates such as organic material and water were desorbed. The specimen was thereafter held under 5 vol % ammonia/helium at 100° C. for 15 minutes to adsorb ammonia on the specimen and then contacted with steam at 100° C. to remove excess ammonia to obtain an ammonia-adsorbing aluminosilicate. Subsequently, the temperature of the ammonia-adsorbing aluminosilicate was raised at 10° C./min in a helium atmosphere, and the amount of ammonia desorbed at 100 to 800° C. was detected by mass spectrometry. The ammonia desorption amount per unit weight is shown as the entirety acid content of aluminosilicate in Table 1.

(Outer Surface Acid Content)

After allowing the specimen aluminosilicate in an amount of 30 mg to stand and dry at 500° C. for 1 hour in vacuum, adsorbates such as organic material and water were desorbed. The specimen was thereafter held under 100% pyridine vapor at 150° C. for 15 minutes to adsorb pyridine on the specimen, and excess pyridine was then removed by exhausting under decompression and a helium flow (by exhausting under decompression to the extent that the pyridine adsorbed on the acid site of zeolite does not desorb, and passing through a helium flow) to obtain a pyridine-adsorbing aluminosilicate. Subsequently, the temperature of the pyridine-adsorbing aluminosilicate was raised at 10° C./min in a helium atmosphere, and the amount of pyridine desorbed at 150 to 800° C. was detected by mass spectrometry. The pyridine desorption amount per unit weight is shown as the outer surface acid content of aluminosilicate in Table 1. Also, the ratio of the outer surface acid content to the entirety acid content is shown in Table 1.

<Reaction>

Examples 1 to 4 and Comparative Example 1

In the reaction, an atmospheric fixed-bed flow reactor was used, and a mixture of 100 mg of the aluminosilicate of each of Preparation Examples 1 to 5 and 400 mg of quartz sand was packed in a quartz-made reaction tube having an inner diameter of 6 mm. A mixed gas containing 30 vol % of ethylene and 70 vol % of nitrogen was supplied to the reactor such that the weight space velocity of ethylene became 0.73 $Hr^{-1}$, and the reaction was allowed to proceed at 400° C. and 0.1 MPa. After the start of reaction, analysis of the product by gas chromatography was performed, that is, the product was analyzed after 2.75 hours in the case of the unmodified catalyst (Comparative Example 1) and analyzed after 1.92 hours in the case of the modified catalyst (Examples 1 to 4). The results are shown in Table 1.

Examples 5 and 6

In the reaction, an atmospheric fixed-bed flow reactor was used, and a mixture of 100 mg of the aluminosilicate of Preparation Example 1 and 400 mg of quartz sand was packed in a quartz-made reaction tube having an inner diameter of 6 mm. A mixed gas containing 30 vol % of ethylene and 70 vol % of nitrogen was supplied to the reactor such that the weight space velocity of ethylene became 0.36 $Hr^{-1}$, and the reaction was allowed to proceed at 350° C. and 0.1 MPa. The product was analyzed by gas chromatography 1.92 hours and 3.17 hours after the start of reaction. The results are shown in Table 1.

TABLE 1

| | Example 1 | Example 2 | Example 3 | Example 4 | Example 5 | Example 6 | Comparative Example 1 |
|---|---|---|---|---|---|---|---|
| Aluminosilicate | Preparation Example 1 | Preparation Example 2 | Preparation Example 3 | Preparation Example 4 | Preparation Example 1 | Preparation Example 1 | Preparation Example 5 |
| Treatment method | silylation treatment | silylation treatment | steam treatment | calcium carbonate mixed steam treatment | silylation treatment | silylation treatment | — |
| Silylating agent at silylation | Tetraethoxy silane | Dimethoxy dimethylsilane | — | — | Tetraethoxy silane | Tetraethoxy silane | — |
| Outer surface acid content (mmol/g) | 0.008 | 0.01 | 0.007 | 0.01 | 0.008 | 0.008 | 0.037 |

TABLE 1-continued

|  | Example 1 | Example 2 | Example 3 | Example 4 | Example 5 | Example 6 | Comparative Example 1 |
|---|---|---|---|---|---|---|---|
| Entirety acid content (mmol/g) | 0.46 | 0.44 | 0.2 | 0.35 | 0.46 | 0.46 | 0.62 |
| Ratio of outer surface acid content to entirety acid content (%) | 1.7 | 2.3 | 3.5 | 2.9 | 1.7 | 1.7 | 6.0 |
| Ethylene conversion (%) | 38.6 | 45.8 | 48.5 | 39.4 | 89.9 | 58.7 | 39.1 |
| Propylene selectivity (%) | 87.6 | 81.2 | 83 | 80.6 | 84.9 | 91.4 | 62.1 |
| Butene selectivity (%) | 4.8 | 6.1 | 10.6 | 9.8 | 3.7 | 1.9 | 15.3 |
| $C_5+$ selectivity (%) | 2.1 | 7.1 | 2.2 | 4.6 | 2.3 | 1.2 | 9.6 |
| Paraffin selectivity (%) | 5.5 | 5.5 | 4.2 | 4.2 | 9.1 | 5.5 | 4.2 |
| Aromatic compound selectivity (%) | 0.0 | 0.0 | 0.0 | 0.8 | 0.0 | 0.0 | 0.0 |

It is seen from the results in Table 1 that the catalysts of Examples 1 to 4 are high in the propylene selectivity and low in the butene selectivity, $C_5+$ selectivity and paraffin selectivity as compared with the catalyst of Comparative Example 1.

Also, it is seen from the results in Table 1 that in the case of the catalysts of Examples 5 and 6, a high propylene selectivity of 80% or more can be obtained, despite a high ethylene conversion of 50% or more.

While the present invention has been described in detail and with reference to specific embodiments thereof, it will be apparent to one skilled in the art that various changes and modifications can be made therein without departing from the spirit and scope of the present invention. This application is based on Japanese Patent Application (Patent Application No. 2009-113596) filed on May 8, 2009, the contents of which are incorporated herein by way of reference.

Industrial Applicability

By using the catalyst of the present invention, propylene can be produced with high selectivity while suppressing the selectivity for $C_4$ or greater components in a process of producing propylene from ethylene.

The invention claimed is:

1. A process of producing propylene comprising contacting ethylene with a catalyst to form propylene, wherein:
   the catalyst comprises a zeolite as an active ingredient;
   an acid content in the outer surface of the zeolite is 5% or less based on an acid content of the entire zeolite;
   the acid content in the outer surface is measured by allowing a substance, capable of selectively adsorbing on acid sites of the zeolite and incapable of intruding into the inside of a micropore of the zeolite, to adsorb on the zeolite, and quantitatively determining the adsorption amount;
   the acid content of the entire zeolite is measured by allowing a substance, capable of selectively adsorbing on acid sites of the zeolite and intruding also into the inside of the micropore, to adsorb on the zeolite, and quantitatively determining the adsorption amount; and said zeolite has a pore size of less than 0.5 nm.

2. The process of claim 1, wherein said acid content in the outer surface of the zeolite is represented by a pyridine desorption amount defined by the following (I):
   (I) a pyridine desorption amount per zeolite unit weight at 150 to 800° C. measured by a temperature-programmed desorption method at a temperature rising rate of 10° C./min on a pyridine-adsorbing zeolite that is obtained by drying a zeolite in vacuum at 500° C. for 1 hr as a pretreatment, contacting the pretreated zeolite with pyridine vapor at 150° C. to adsorb pyridine on the zeolite, and removing excess pyridine from said zeolite at 150° C. by exhausting under decompression and a helium flow.

3. The process of claim 1, wherein said acid content of the entire zeolite is represented by an ammonia desorption amount defined by the following (II):
   (II) an ammonia desorption amount per zeolite unit weight at 100 to 800° C. measured by a temperature-programmed desorption method at a temperature rising rate of 10° C./min on an ammonia-adsorbing zeolite that is obtained by drying a zeolite under an a helium flow at 500° C. for 1 hr as a pretreatment, contacting the pretreated zeolite with 5 vol% ammonia/helium at 100° C. to adsorb ammonia on the zeolite, and contacting the obtained zeolite with steam at 100° C. to remove excess ammonia from said zeolite.

4. The process of claim 1, wherein said zeolite has an oxygen 8-membered ring structure or an oxygen 9-membered ring structure.

5. The process of claim 1, wherein a framework structure of said zeolite is a CHA structure.

6. The process of claim 1, wherein the outer surface of said zeolite is silylated.

7. The process of in claim 1, wherein said zeolite is steam-treated.

8. The process of claim 7, wherein a temperature of said steam treatment is from 400 to 700° C.

9. The process of claim 7, wherein said zeolite is steam-treated after mixing with a compound containing an alkaline earth metal.

* * * * *